(12) United States Patent
Lu et al.

(10) Patent No.: US 8,126,244 B2
(45) Date of Patent: Feb. 28, 2012

(54) USER INTERFACE FOR POLYP ANNOTATION, SEGMENTATION, AND MEASUREMENT IN 3D COMPUTED TOMOGRAPHY COLONOGRAPHY

(75) Inventors: Le Lu, East Norriton, PA (US); Adrian Barbu, Tallahassee, FL (US); Matthias Wolf, Coatesville, PA (US); Sarang Lakare, Chester Springs, PA (US); Luca Bogoni, Philadelphia, PA (US); Marcos Salganicoff, Bala Cynwyd, PA (US); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 826 days.

(21) Appl. No.: 12/231,771

(22) Filed: Sep. 5, 2008

(65) Prior Publication Data
US 2009/0080747 A1 Mar. 26, 2009

Related U.S. Application Data

(60) Provisional application No. 60/974,102, filed on Sep. 21, 2007.

(51) Int. Cl.
*G06K 9/34* (2006.01)
(52) U.S. Cl. .................. 382/131; 382/128; 382/173
(58) Field of Classification Search .............. 382/128, 382/131, 173
See application file for complete search history.

(56) References Cited

U.S. PATENT DOCUMENTS

| | | | |
|---|---|---|---|
| 5,458,111 A * | 10/1995 | Coin | 600/560 |
| 6,212,420 B1 * | 4/2001 | Wang et al. | 600/407 |
| 6,331,116 B1 | 12/2001 | Kaufman et al. | |
| 6,514,082 B2 | 2/2003 | Kaufman et al. | |
| 6,928,314 B1 * | 8/2005 | Johnson et al. | 600/407 |
| 6,947,784 B2 * | 9/2005 | Zalis | 600/425 |
| 7,148,887 B2 | 12/2006 | Kaufman et al. | |
| 7,260,250 B2 * | 8/2007 | Summers et al. | 382/128 |
| 7,333,644 B2 * | 2/2008 | Jerebko et al. | 382/128 |
| 7,346,209 B2 * | 3/2008 | Gokturk et al. | 382/159 |
| 7,369,638 B2 * | 5/2008 | Kiraly et al. | 378/4 |
| 7,379,572 B2 * | 5/2008 | Yoshida et al. | 382/128 |

(Continued)

OTHER PUBLICATIONS

J. Yao, et al., "Colonic Polyp Segmentation in CT Colonography-Based on Fuzzy Clustering and Deformable Models", IEEE, 2004.

(Continued)

*Primary Examiner* — Allen C. Ho

(57) ABSTRACT

A method and system for providing a user interface for polyp annotation, segmentation, and measurement in computer tomography colonography (CTC) volumes is disclosed. The interface receives an initial polyp position in a CTC volume, and automatically segments the polyp based on the initial polyp position. In order to segment the polyp, a polyp tip is detected in the CTC volume using a trained 3D point detector. A local polar coordinate system is then fit to the colon surface in the CTC volume with the origin at the detected polyp tip. Polyp interior voxels and polyp exterior voxels are detected along each axis of the local polar coordinate system using a trained 3D box. A boundary voxel is detected on each axis of the local polar coordinate system based on the detected polyp interior voxels and polyp exterior voxels by boosted 1D curve parsing using a trained classifier. This results in a segmented polyp boundary. The segmented polyp is displayed in the user interface, and a user can modify the segmented polyp boundary using the interface. The interface can measure the size of the segmented polyp in three dimensions. The user can also use the interface for polyp annotation in CTC volumes.

27 Claims, 12 Drawing Sheets

U.S. PATENT DOCUMENTS

| | | | | |
|---|---|---|---|---|
| 7,440,601 | B1 * | 10/2008 | Summers et al. | 382/128 |
| 7,454,045 | B2 * | 11/2008 | Yao et al. | 382/128 |
| 7,492,968 | B2 * | 2/2009 | Jerebko et al. | 382/300 |
| 7,630,529 | B2 * | 12/2009 | Zalis | 382/128 |
| 7,634,133 | B2 * | 12/2009 | Jerebko et al. | 382/173 |
| 2006/0239552 | A1 | 10/2006 | Tu et al. | |

OTHER PUBLICATIONS

A. Jerebko, et al., "Symmetric Curvature Patterns for Colonic Polyp Detection", MICCAI, 2006.

Taylor et al., "CT Colonography: Automated Measurement of Colonic Polyps Compared With Manual Techniques—Human in Vitro Studt", Radiology, vol. 242, No. 1, Jan. 1, 2007, pp. 120-128.

Kiraly et al., "A Fast Method for Colon Polyp Detection in High-Resolution CT Data", International Congress Series, vol. 1268, 2004, pp. 983-988.

International Search Report including Notification of Transmittal of the International Search Report, International Search Report, and Written Opinion of the International Searching Authority, dated Mar. 3, 2009.

* cited by examiner ically Colonography

USER INTERFACE FOR POLYP ANNOTATION, SEGMENTATION, AND MEASUREMENT IN 3D COMPUTED TOMOGRAPHY COLONOGRAPHY

This application claims the benefit of U.S. Provisional Application No. 60/974,102, filed Sep. 21, 2007, the disclosure of which is herein incorporated by reference.

BACKGROUND OF THE INVENTION

The present invention relates to 3D computed tomography (CT) colonography, and more particularly, to providing a user interface for polyp annotation, segmentation, and measurement in 3D CT colonography.

Colon cancer is the number two cause of cancer death in men and women combined, but it is one of the most preventable cancers because doctors can identity and remove precancerous growths known as polyps. 3D CT colonography (CTC), or virtual colonoscopy, is emerging as a powerful polyp screening tool because of its non-invasiveness, low cost, and high sensitivity. 3D CTC visualizes the colon, and allows a physician to navigate the colon to search for polyps. However, the physician needs to manually adjust the navigation speed and change the angle in order to see a polyp clearly. For example, a polyp may be hidden in a colonic fold and thus could be missed during the physician's visual inspection. Accordingly, there has been much research in computer aided detection (CAD) of polyps in CTC, and several such CAD systems have been proposed. Once a polyp is detected either manually or automatically, the polyp is measured and classified by a physician. However, there is a large variability in physician's measurements of polyps. Therefore, an accurate, consistent, and automated method for polyp measurement is desirable.

Polyp segmentation is defined as extracting as isolating a polyp from the colon wall at a given location. In addition to its significant value for polyp measurement in clinical practice, polyp segmentation is also important for computer aided detection of polyps. Polyp segmentation is a challenging task because polyps are abnormal growths from the colon wall and the "expected" segmentations are often a semantic, perceptual boundary with low imaging contrast support. Furthermore, there are multiple shape categories of polyps, such as sessile, pedunculated, flat, etc., with a large 3D shape/appearance variation. Conventional polyp segmentation methods utilize unsupervised segmentation or clustering in 3D data volumes. Such methods include, fuzzy clustering, deformable model or snakes, variational level-set method, and heuristic surface curvature constraints. These unsupervised approaches work well for up to 70% of polyps due to unclear polyp/nonpolyp boundaries, large within-class polyp appearance/shape variations, or limited heuristic shape assumptions. Accordingly, an automatic polyp segmentation method having increased accuracy is desirable.

BRIEF SUMMARY OF THE INVENTION

The present invention provides a method and system for providing an interface for polyp annotation, segmentation, and measurement in 3D computed tomography colonography (CTC) volumes.

In one embodiment of the present invention, an initial polyp location in a CTC volume is received by a user interface. The interface automatically segments the polyp based on the initial polyp position and displays the segmented polyp. In order to segment the polyp, a polyp tip is detected in the CTC volume using a trained 3D point detector. A local polar coordinate system is then fit to the colon surface in the CTC volume with the origin at the detected polyp tip. Polyp interior voxels and polyp exterior voxels are detected along each axis of the local polar coordinate system using a trained 3D box. A boundary voxel is detected on each axis of the local polar coordinate system based on the detected polyp interior voxels and polyp exterior voxels by boosted 1D curve parsing using a trained classifier. The segmented polyp can be displayed in the user interface by displaying 2D cutting planes corresponding to axes of the local polar coordinate system. A user can modify the segmented polyp boundary using the interface, and the interface re-segments the polyp based on the user input. The interface can measure the size of the segmented polyp in three dimensions.

These and other advantages of the invention will be apparent to those of ordinary skill in the art by reference to the following detailed description and the accompanying drawings.

DETAILED DESCRIPTION

The present invention is directed to an interface for polyp annotation, segmentation, and measurement in 3D computed tomography colonography (CTC) volumes. Embodiments of the present invention are described herein to give a visual understanding of the polyp annotation, segmentation, and measurement. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention are directed to a semi-automatic user interface for 3D polyp boundary annotation, segmentation and dimensioning measurement in 3D CTC. The user interface offers increased flexibility and freedom in terms of CTC volume 3D navigation by fitting a set of axes of polar coordinates onto user identified or automatically detected polyp locations. The traditional orthonormal (XY, YZ, ZX planes) 2D slices of a 3D CTC volume are significantly enhanced with 2D radial cut planes, which can be centered on any user selection point. The user interface can be used for semi-automatic user annotation with machine learning segmentation, as apposed to fully manual annotation in previous systems. The trained learning segmentation subsystem can automatically generate an initial polyp segmentation boundary, where experienced users can easily modify the polyp segmentation boundary using expert knowledge to improve the segmented polyp boundary. For less-experienced users, the automatic segmentation functionality can serve as a trainer to guide annotation. This not only eliminates the ambiguity of labeling polyps for new users, but also saves time to train them. By using this interface, users can modify the segmented polyp boundary by simply moving the output polyp boundary points to more accurate positions when necessary. The three axes of segmented 3D polyp surface can be automatically calculated. Conventional labeling systems can only find the largest polyp axis or select from multiple axis hypotheses by experts using a trail-and-compare strategy. Accordingly, the interface produces more accurate polyp size measurements than conventional labeling systems.

In addition to the features described above, the polyp annotation, segmentation, and measurement interface can also provide various other functions, such as user-controlled contour smoothing, contrast visibility controlling, easier access to CTC volume sequences, and separately staged polyp processing display for performance/error analysis and volume visualization under different modalities (i.e., original volume, voxel-based gradient surface volume, mesh-based surface volume).

Figure 1:
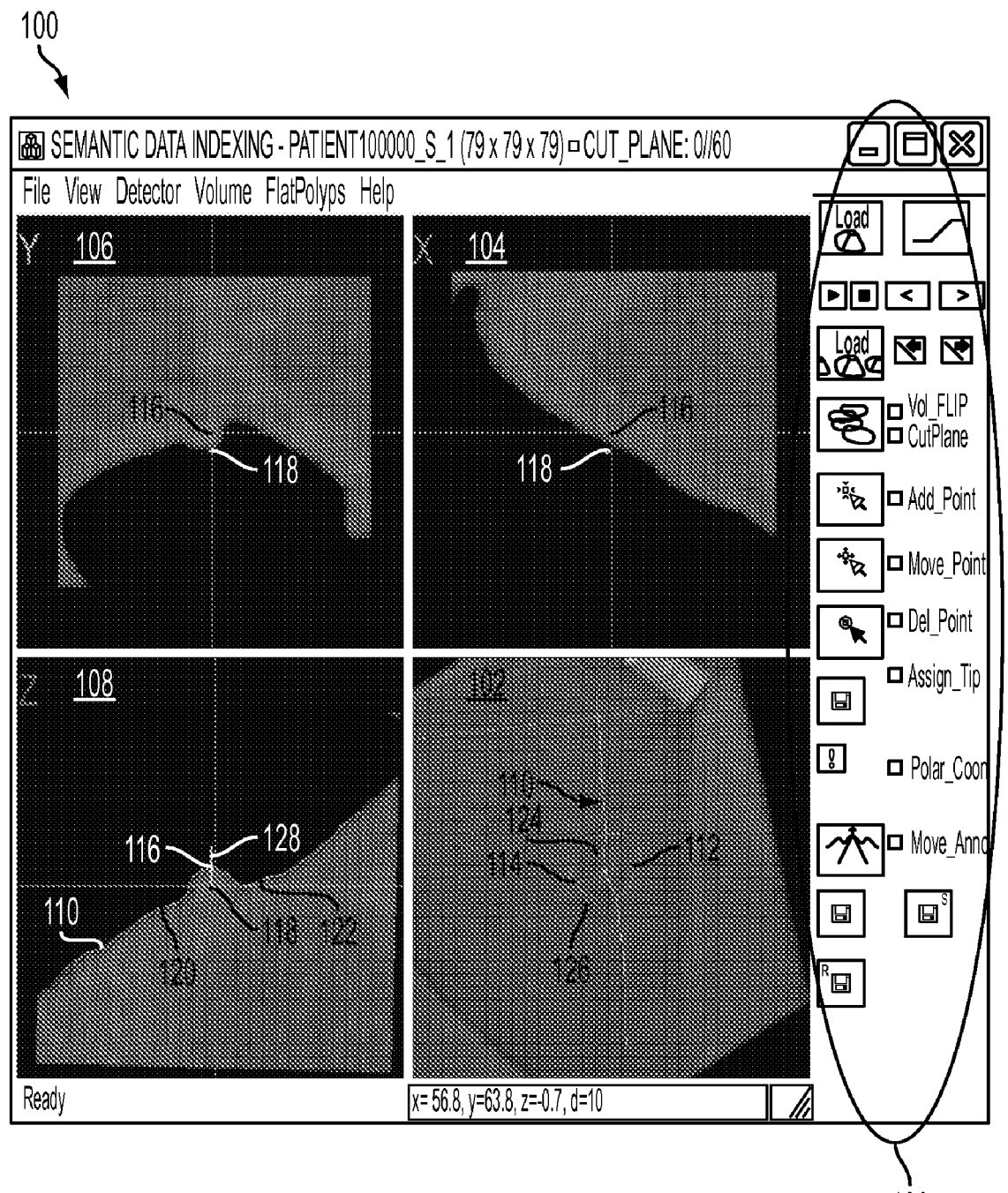
FIG. 1 illustrates a snapshot of a polyp annotation, segmentation, and measurement interface according to an embodiment of the present invention.

The interface can be implemented as a graphical user interface. Such a graphical user interface can be implemented by a computer system executing computer executable instructions stored on a computer readable medium. FIG. 1 illustrates a snapshot of a polyp annotation, segmentation, and measurement interface according to an embodiment of the present invention. As illustrated in FIG. 1, the interface 100 displays various views in images 102, 104, 106, and 108 of a CTC volume. The interface can be used for polyp annotation, segmentation and measurement in a CTC volume. Image 102 is a 3D view of the CTC volume. The 3D view 102 of the CTC volume shows a polar coordinate axis 110 of a local polar coordinate system fit to the colon surface, as well as an annotated polyp boundary 112 and, a segmented polyp boundary 114, and polyp axes 124 and 126 calculated to measure the dimensions of the segmented polyp. Images 104, 106, and 108 are 2D radial cutting planes of the 3D CTC volume along the polar coordinate axis 110 in x, y, and z directions, respectively, centered on an initial polyp location 116. A polyp tip 118 detected in the automatic polyp segmentation is shown in each of the cutting planes 104, 106, and 108. Cutting plane 108 shows a normal vector 128 to the detected polyp tip 118, as well as annotated polyp boundary points 120 and 122 along the polar coordinate axis 110. The interface 100 also includes various controls 130, such as buttons and check-boxes, that allow a user to control the interface, for example to browse CTC volumes, annotate, segment, and measure polyps, smooth segmentation results, and control how volumes and segmentation results are displayed.

Figure 2:
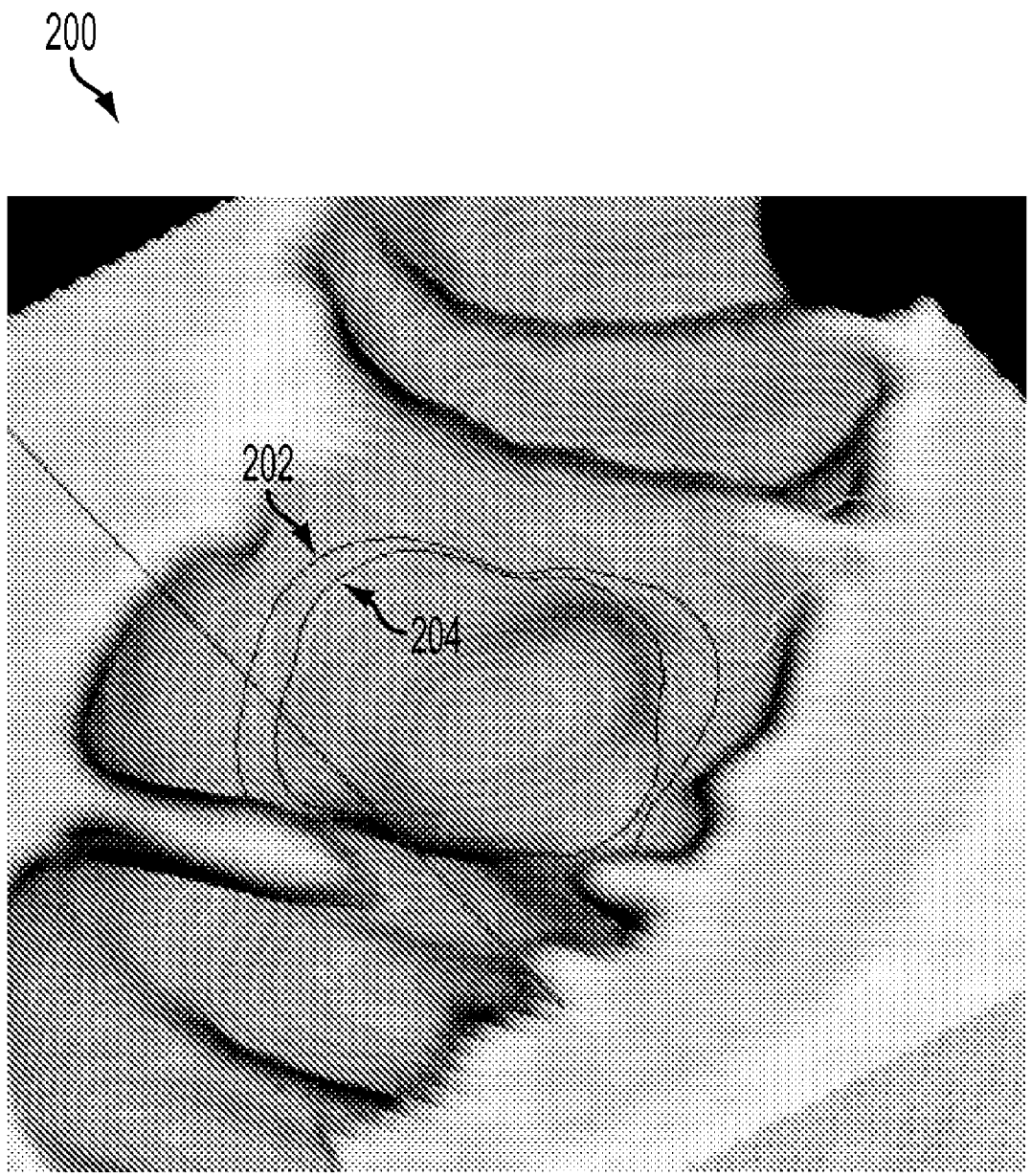
FIG. 2 illustrates exemplary polyp segmentation in a CTC volume.
Figure 3:
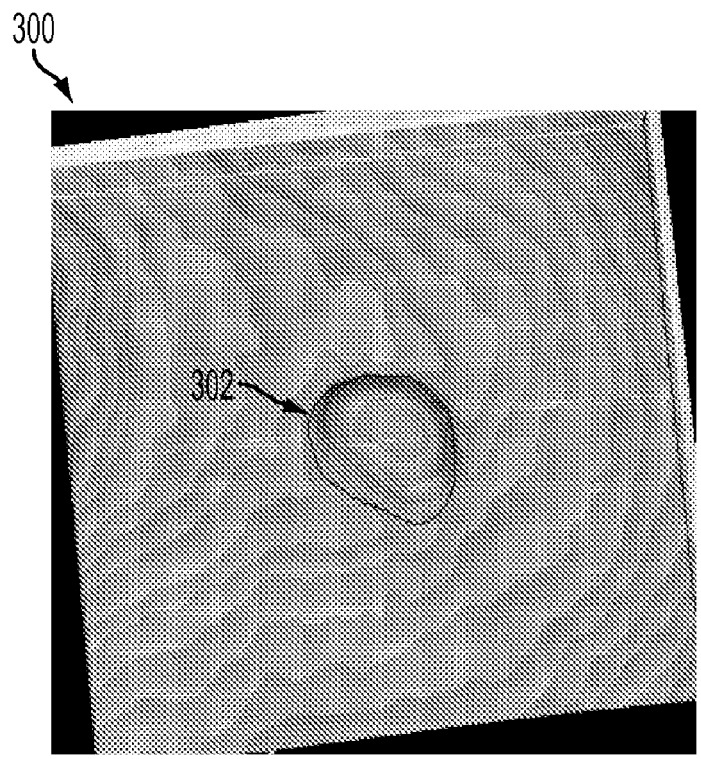
FIG. 3 illustrates exemplary polyp segmentation results.
Figure 3:
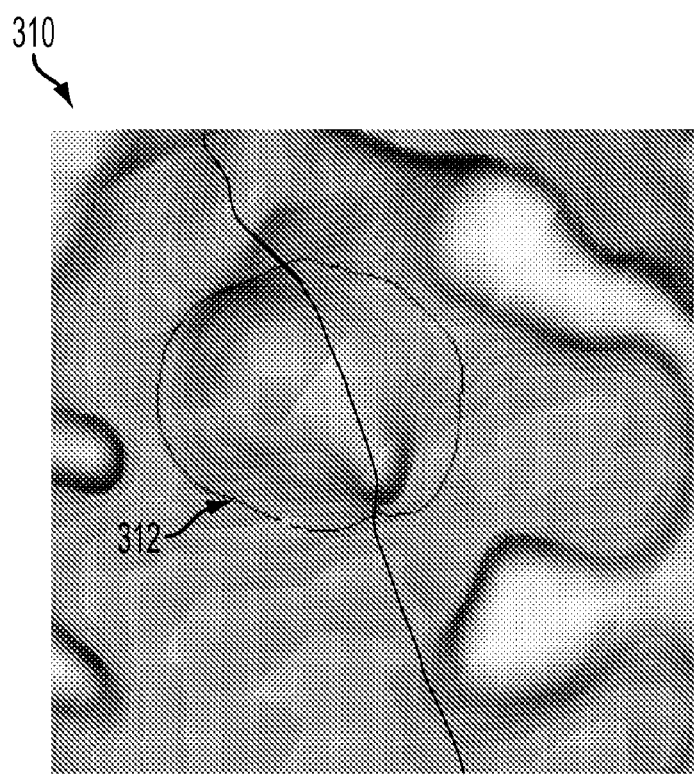

FIG. 2 illustrates exemplary polyp segmentation in a CTC volume. Image 200 is a mesh-based 3D colon surface model constructed using the well known Marching Cubes algorithm from a 3D CTC volume. Such a mesh-based colon surface model can be generated and displayed by the polyp annotation, segmentation, and measurement interface during the automatic segmentation of a polyp. As shown in image 200, curve 202 is an expert polyp boundary annotation separating polyp interior voxels from polyp exterior voxels, and curve 204 is a segmented polyp boundary segmented using the automatic segmentation of the interface according to an embodiment of the present invention. The set of surface voxels inside the closed curves 202 and 204 is considered as the labeled and classified (segmented) polyp region, respectively. In image 200, the difference between the annotated curve 202 and the segmented curve 204 is within an acceptable inter-reader variability among clinic experts. FIG. 3 illustrates exemplary polyp segmentation results. As illustrated in FIG. 3, images 300 and 310 are colon surface models of CTC volumes showing segmenting polyp boundaries 302 and 312, respectively. The polyp boundaries 302 and 312 are segmented from CTC volume using the automatic segmentation functionality of the interface. As shown in FIGS. 2 and 3, 3D polyps can have large shape variations in CTC volumes and the automatic segmentation works for various shapes of 3D polyps.

Figure 4:
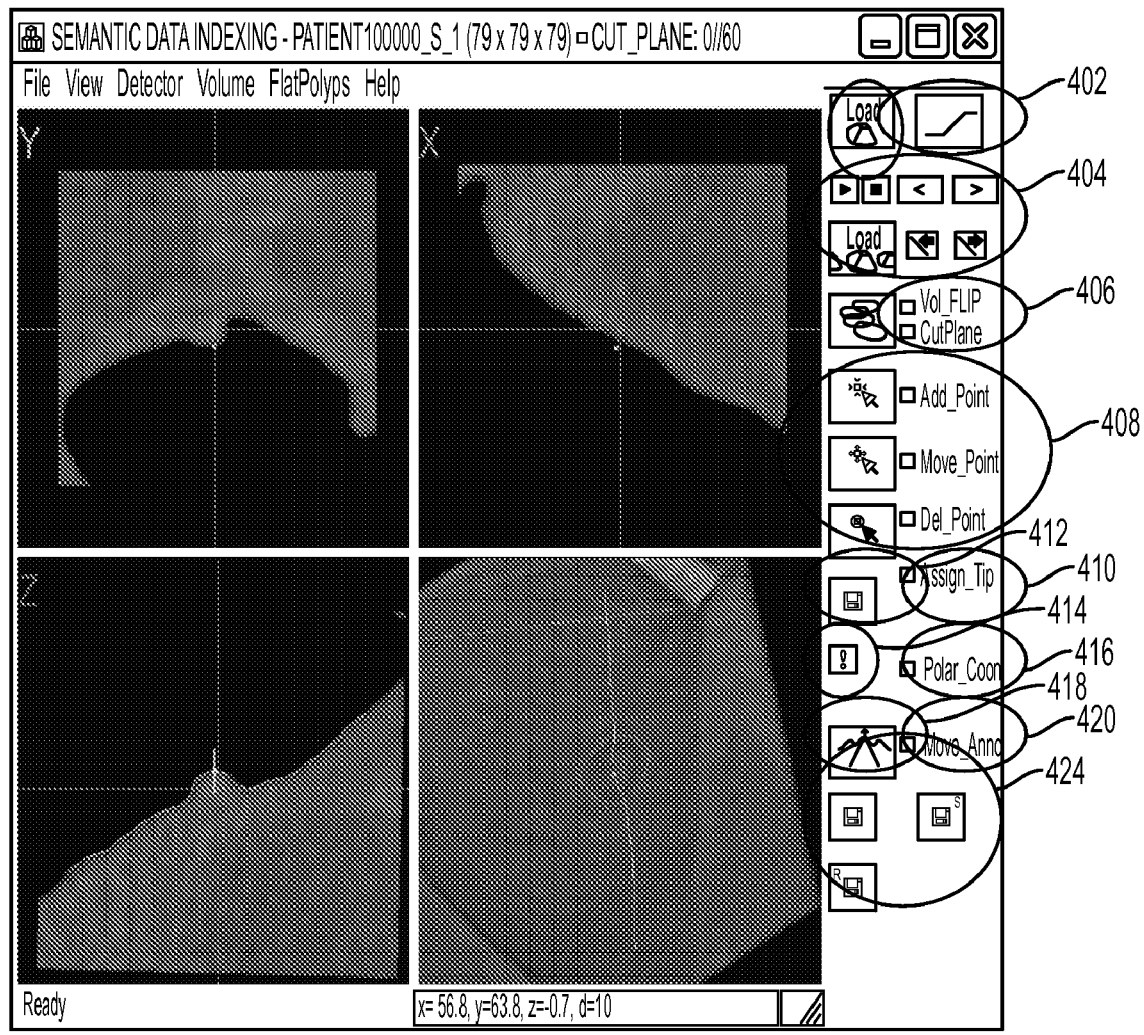
FIG. 4 illustrates user controls of the polyp annotation, segmentation, and measurement interface according to an embodiment of the present invention.
Figure 5:
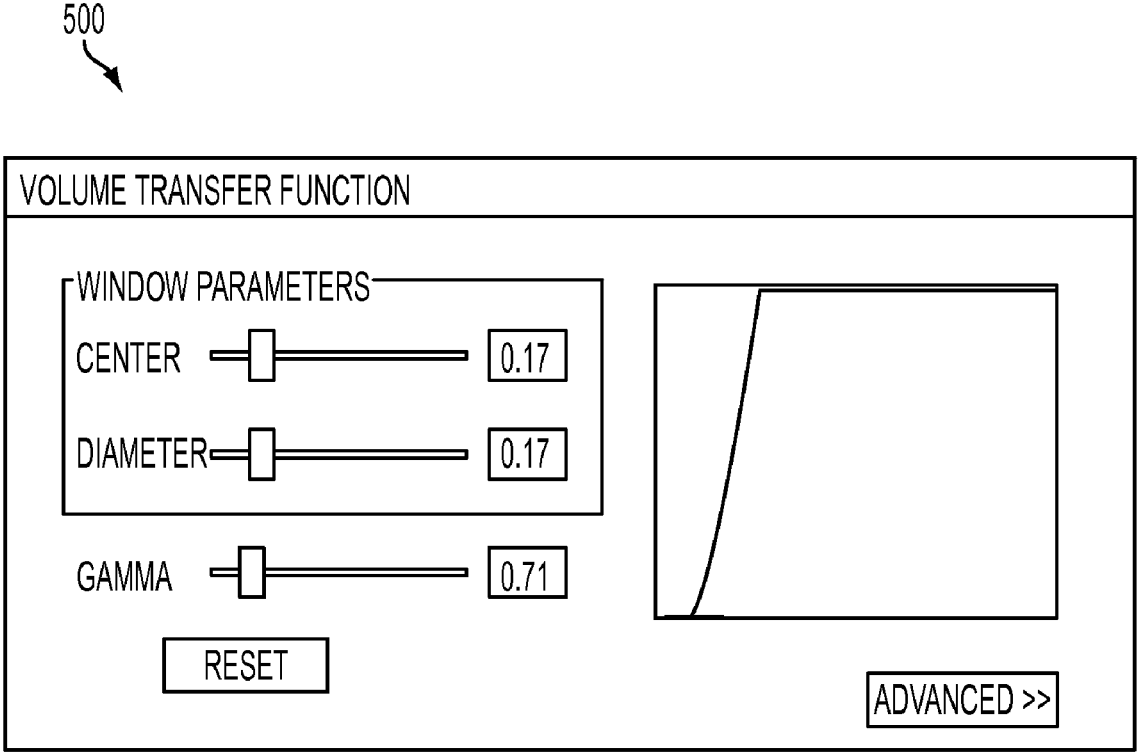
FIG. 5 illustrates an exemplary contrast pop-up window.

FIG. 4 illustrates user controls of the polyp annotation, segmentation, and measurement interface according to an embodiment of the present invention. As described above and illustrated in FIG. 1, the interface 100 has controls 130 that provide various functionalities that allow a user to control the interface. FIG. 4 shows an exemplary embodiment of the controls and the functionalities provided to the interface by such controls. As illustrated in FIG. 4, a contrast control 402 allows a user to adjust a contrast of displayed image data in order to control visibility. According to a possible implementation, in response to a user selection of the contrast control 402, the interface may launch a pop-up window to allow the user to control the contrast. FIG. 5 illustrates an exemplary contrast pop-up window. As illustrated in FIG. 5, a pop-contrast window 500 allows a user to adjust window parameters (center and diameter), as well as the gamma distribution of the volume transfer function.

Returning to FIG. 4, volume browsing controls 404 allow a user to load a single CTC volume or a sequence of CTC volumes to the interface, and browse through the CTC volumes, for example using right and left arrow buttons. Volume switching and Cutplane controls 406 allow a user to switch between flipping through different volumes of a CTC volume sequence or different cutting planes of a single CTC volume as the displayed images. B-spline annotation controls 408 allow a user to edit control points of B-spline based annotation. A polyp tip annotation control 410 allows a user to switch to an editing mode for annotating the polyp tip by clicking in x, y, or z radial planes. Save control 412 controls the interface to save the polyp tip annotation. Polar coordinate control 416 allows a user to switch polar coordinates on and off of the displayed images. A polyp boundary annotation control 420 allows a user to switch to an editing mode for annotating the polyp boundary. Controls 424 control the interface to save, smooth, and reload the polyp boundary annotation. A polyp segmentation button 418 controls the interface to execute the embedded automatic learning-based polyp segmentation, and an alternative polyp segmentation button 414 controls the interface to execute an alternative polyp segmentation method. It is to be understood that the controls and functionalities described herein are merely exemplary, and the present invention is not limited thereto.

Figure 6:
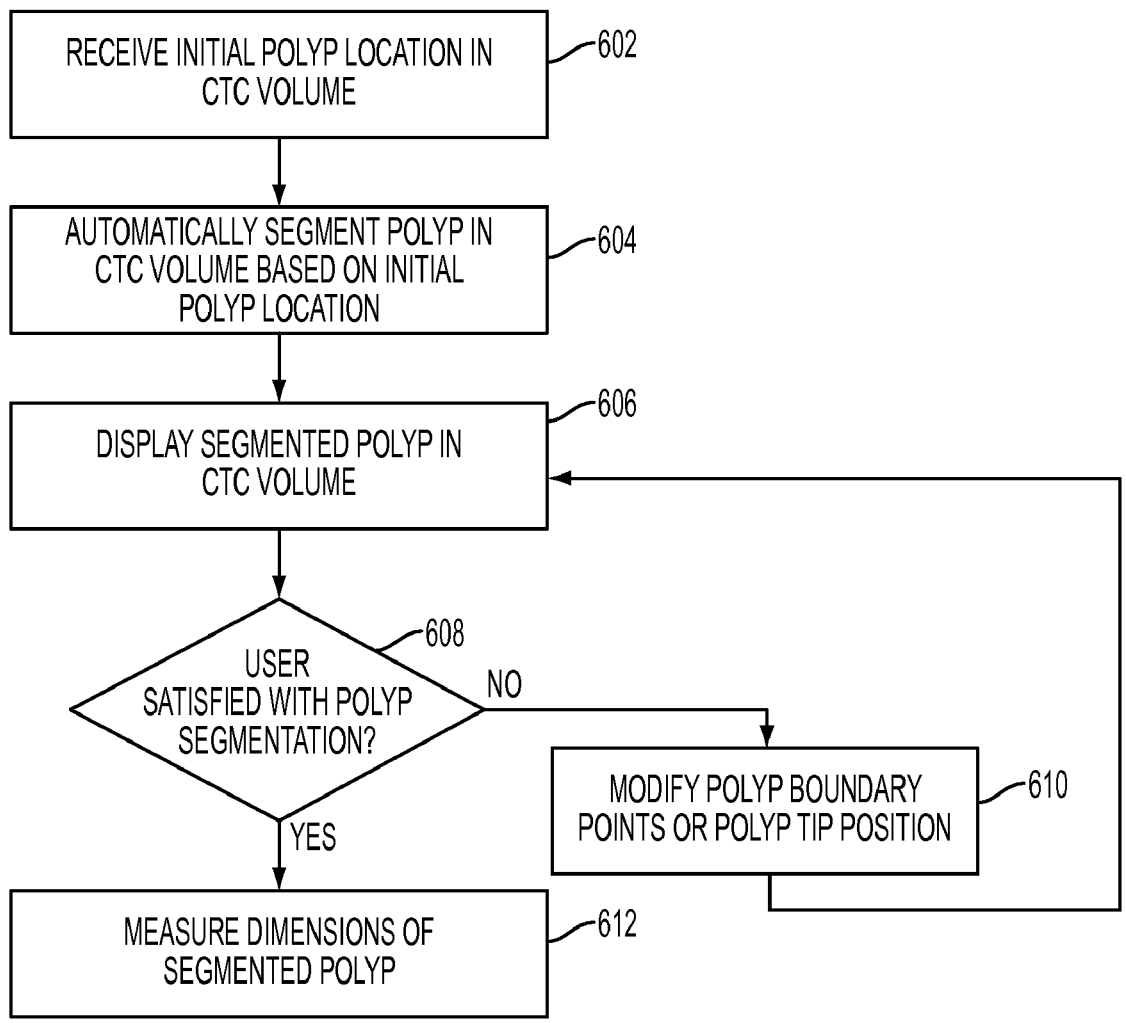
FIG. 6 illustrates a method for polyp segmentation and measurement in a CTC volume using an interface according to an embodiment of the present invention.

FIG. 6 illustrates a method for polyp segmentation and measurement in a CTC volume using an interface according to an embodiment of the present invention. As illustrated in FIG. 6, at step 602, an initial polyp location in CTC volume is received. The CTC volume can be received directly from an image acquisition device, or can be received by loading a CTC volume stored in memory, storage, or other computer readable medium of a computer system. The initial polyp location can be manually selected by a user using the user interface. For example, the CTC volume can be displayed by the interface, and a user can use an input device to select an initial polyp location using the editing or annotating functionality of the interface. Alternatively, the initial polyp location can be a polyp detection result of a computer aided detection (CAD) system. In a possible embodiment, the CAD system can be part of the interface, such that the CAD detection of the initial polyp location is performed in response to a user input to the interface selecting polyp detection by the CAD system.

At step 604, the polyp is automatically segmented in the CTC volume based on the initial polyp location. The interface utilizes machine-learning based segmentation with stored classifiers to segment a boundary of the polyp. The automatic polyp segmentation may be performed in response to a user input, such as a user selecting a specified control of then interface (e.g., polyp segmentation button 418 of FIG. 4). Polyp segmentation, as performed in embodiments of the present invention, is the extraction of the polyp boundary in the CTC volume given an initial position. In order to segment a polyp, the polyp tip is detected as a voxel on the polyp surface by a 3D point detector, followed by clustering and centering. A polar coordinate system is then constructed using the detected polyp tip as its origin with a set of evenly sampled radial axes, which are 1D curves on the colon surface. The polyp boundary learning is performed along these 1D sampling axes using two-layered stacking learning using a 3D box detector and 1D curve parsing detector to effectively determine which portion of the curve is polyp and which portion of the curve is non-polyp. The binary probabilistic boundary decisions on all 1D curves/axes are assembled jointly based on their axis connectivity in the polar coordinates to generate a complete 3D polyp segmentation.

Figure 7:
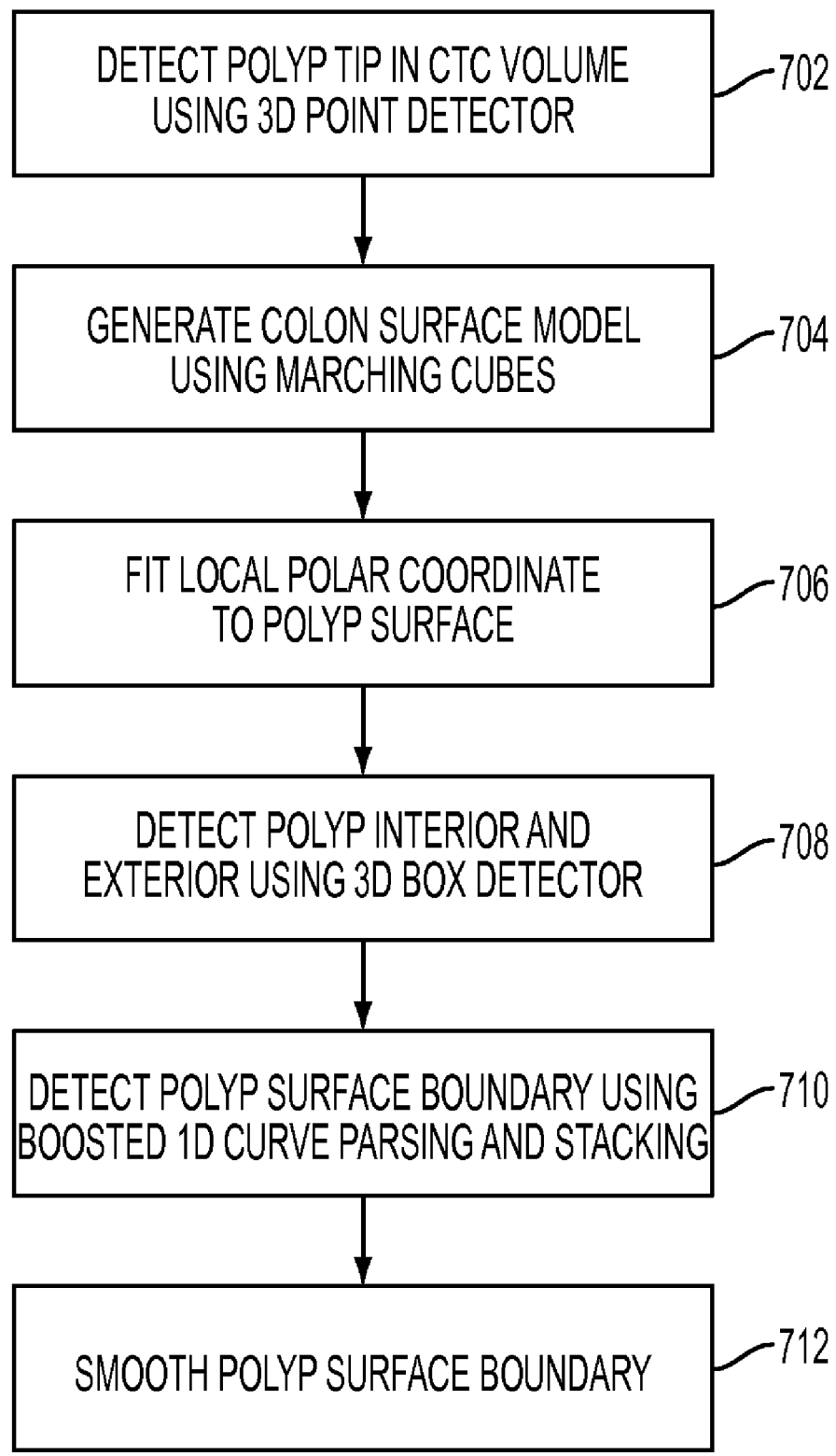
FIG. 7 illustrates a method for polyp segmentation in a CTC volume according to an embodiment of the present invention.
Figure 8:
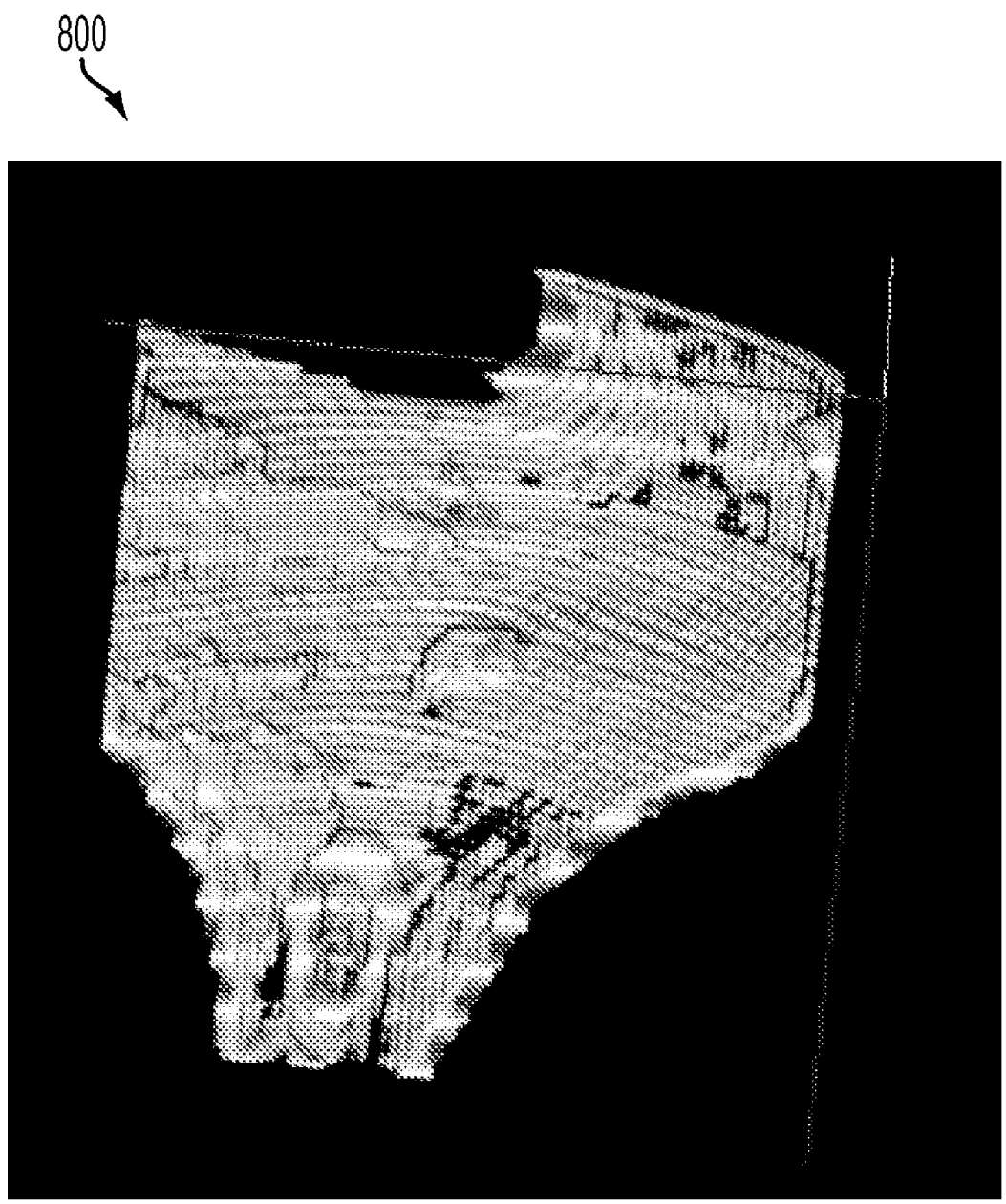
FIG. 8 illustrates an exemplary gradient based surface for detecting colon surface voxels in a CTC volume.

FIG. 7 illustrates a method for polyp segmentation in a CTC volume according to an embodiment of the present invention. The method of FIG. 7 can be used by the interface to perform the automatic polyp segmentation of step 604. At step 702, a polyp tip is detected in the CTC volume using a 3D point detector. The polyp tip is defined herein as a colon surface voxel inside a polyp region neighboring the initial polyp location, and reasonably close to the center of the polyp region. Since the polyp tip is defined as a colon surface voxel, the search domain for the polyp tip can be limited to the domain of surface voxels (i.e., voxels with non-zero gradients). In order to extract the domain of surface voxels, a gradient surface can be generated, for example using 3D Canny edge detection. FIG. 8 illustrates an exemplary gradient based surface for detecting colon surface voxels in a CTC volume. As illustrated in FIG. 8, image 800 is a gradient based surface image generated from a raw CT data volume using 3D Canny edge detection. According to a possible implementation, the interface can display the gradient based surface image. Once the surface voxels are extracted by generating the gradient surface, the polyp tip detection is performed by classification of surface voxels as polyp tip voxel candidates using a trained 3D point detector, and clustering and centering the polyp tip voxel candidates to determine the polyp tip voxel.

The 3D point detector can be trained as probabilistic boosting tree (PBT) classifier using axis-based steerable features. A PBT classifier is trained by recursively constructing a tree, where each of the nodes represents a strong classifier. Once the strong classifier of each node is trained, the input training data for the node is classified into two sets (positives and negatives) using the learned strong classifier. The two new sets are fed to left and right child nodes respectively to train the left and right child nodes. In this way, the PBT classifier is constructed recursively. The trained classifier (3D point detector) is denoted herein as $PBT_1$. The trained 3D point detector ($PBT_1$) is used to detect polyp tip voxel candidates from the surface voxels of the sub-volume. Accordingly, $PBT_1$ determines a positive-class probability value prob(v) (from 0 to 1) for each surface voxel v of the sub-volume. If prob(v)>$T_1$ for a voxel, where $T_1$ is a first threshold value, then the voxel is classified as a polyp tip voxel candidate.

From all the detected polyp tip voxel candidates $(S\{v\}=\{v\}: prob(v)>T_1)$ in a volume (or sub-volume), one voxel is detected as the polyp tip voxel by clustering and centering. The first threshold value $T_1$ can be determined based on receiver operating characteristics (ROC) of the trained PBT classifier ($PBT_1$). Connected component analysis is applied to partition the set $S\{v\}$ into a list of n clusters $C_1\{v\}, C_2\{v\}, \ldots, C_n\{v\}$. For each of the clusters, a fitness score $P_i = \Sigma_{v \in C_i\{v\}} \{prob(v)\}, i=1,2, \ldots, n$, is calculated, reflecting the overall fitness of that class being a positive polyp tip class. The cluster with the maximal fitness score is selected: $C_j\{v\}$ where $P_j \geq P_i$, $i=1,2, \ldots, n$, and the other clusters are discarded. According to a possible implementation, a 3D multivariate normal distribution based spatial prior $G(v(x,y,z)|\mu,\Sigma)$ can be integrated into $P_i$ to reflect the confidence of the initial polyp position input $\mu$ for the CAD system or manual selection. The geometric mean $\bar{\mu}(x,y,z)$ of the winning cluster $C_j\{v(x,y,z)\}$ is calculated and projected to the colon surface by finding $\bar{v}$ where $dist(\bar{v},\bar{\mu}) \leq dist(v,\bar{\mu})$ and $v \in S\{v\}$. $\bar{v}$ is the detected polyp tip voxel. The detected polyp tip voxel $\bar{v}$ is detected by integrating PBT learned class-conditional information from local (i.e., polyp tip 3D point detection) to semi-global scale (i.e., clustering and centering).

Figure 9:
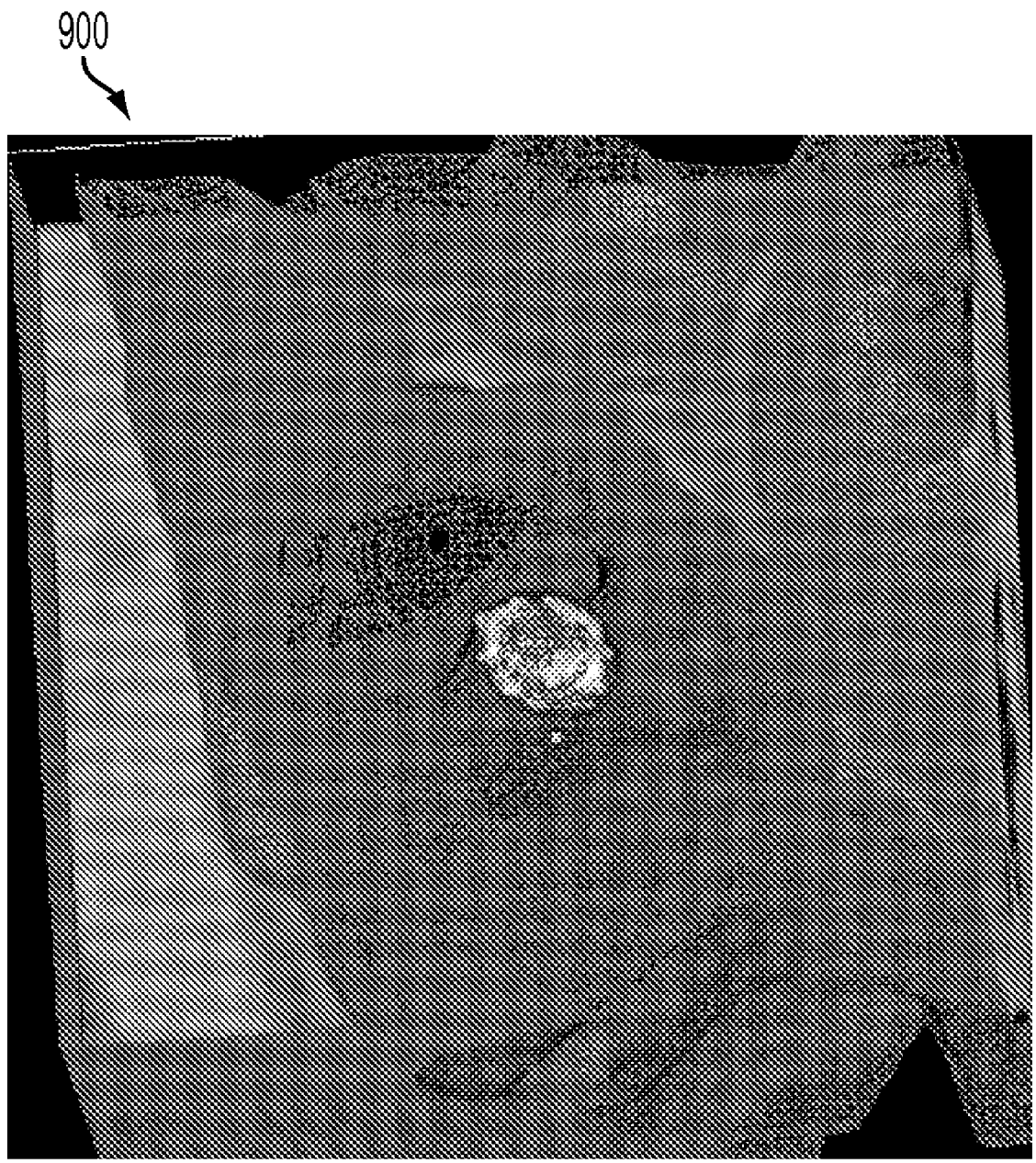
FIG. 9 illustrates an exemplary colon surface model.

Returning to FIG. 7, at step 704, a colon surface model is generated. The colon surface model can be generated using the Marching Cubes algorithm. The Marching Cubes algorithm is a well known method of constructing a polygonal mesh of an isosurface from a 3D field of scalar values or voxels (i.e., a 3D volume) in both medical and geological scans. The Marching Cubes algorithm subdivides a 3D volume space into a series of small cubes. The algorithm then "marches" through each of the cubes by testing the fitness of the current set of corner points against the predefined 15 configurations, and replaces the cube with an appropriate set of polygons. A global mesh is then generated by fusing all the cube polygons while enforcing a smoothness constraint. Since the gradient of the scalar field at each voxel is also the normal vector of a hypothetical isosurface passing from that point, these normals can be interpolated along the edges of each cube to calculate the normals of all the generated vertices. FIG. 9 illustrates an exemplary colon surface model. As illustrated in FIG. 9, image 900 is a mesh-based CTC colon surface model generated from a CTC volume using the Marching Cubes algorithm.

Figure 10:
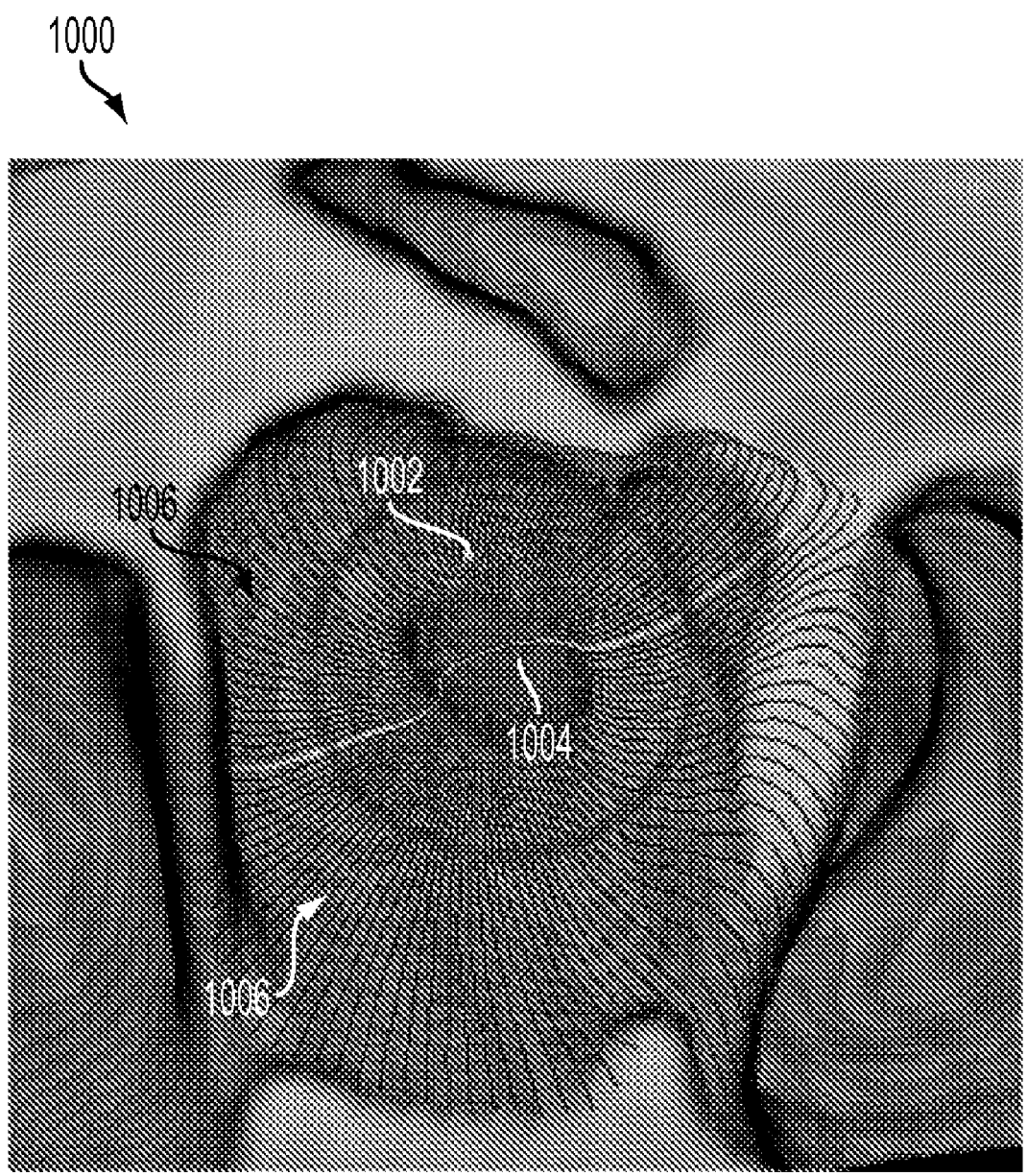
FIG. 10 illustrates exemplary results of filling a local polar coordinate system to a colon surface of a CTC volume.

Returning to FIG. 7, at step 706, a local polar coordinate system is fit to the colon surface. Once the mesh-based colon surface is generated, the polyp tip t is identified as the closest vertex on the mesh from $\bar{v}$. Accordingly, $\bar{v}$ is transferred onto the mesh as t. The local polar coordinate system is generated using t as its origin. Given a normal vector n, at t, two other axes which are orthogonal to n, are defined. In theory, the configuration of these two axes is not unique (i.e., they can be any two axes in $n_t$ s orthogonal plane $P_t$ passing through t which are mutually orthogonal as well), but embodiments of the present invention fix this configuration by enforcing one axis (Y) passing through the intersection point of $P_t$ and a predefined line vector, such as [1,0,z], where z is an arbitrary value. $n_t$ is denoted as axis X, another axis constrained as Y, and axis Z is calculated as the cross product of X and Y. The cutting planes $P_n$ are defined as planes passing through $n_t$ or X, and another line segment Y' in $P_t$ which evenly rotates from Y in a clockwise direction. The axes of the final constructed polar coordinates are the intersected curves between $P_n$ and the colon surface mesh. The coordinates on each are defined based on their geodesic distances from t (the origin) on the corresponding cutting curve or axis. The total number of axes is set as I, and they are spatially ordered in a loop. Axis i is adjacent to axes mod(i−1,I) and mod(i+1,I). FIG. 10 illustrates exemplary results of fitting a local polar coordinate system to a colon surface of a CTC volume. As illustrated in FIG. 10, image 400 shows the initial polyp location 1002, the detected final polyp tip 1004, and the polar coordinates 1006 fit to the volume.

The fitting of a local polar coordinate system, which is a spatially ordered collection of 1D curve axes, is used to represent the 3D polyp surface due to the flexibility and convenient formulation to parameterization. Compared to Conformal mapping, no user indentified 3D-2D correspondences are needed and there is no constraint on 3D surface with disk topology. Furthermore, this representation, which uses a collection of 1D curves as sampling coordinates to model the 3D colon surface shape, decreases the intrinsic dimensionality problem (i.e., 1D vs. 3D modeling). This decomposable formulation makes it feasible to construct or model a large variety of 3D shapes using an assembly of simple 1D curves that are learnable and flexible.

Returning to FIG. 7, at step 708, polyp interior and exterior voxels are detected along each local polar coordinate axis using a 3D box detector. The 3D box detector can be trained as a PBT based classifier, referred to herein as $PBT_2$, using 3D box based steerable features. Boxes are centered at each voxel and aligned with the local gradient surface. Compared with the 3D point detector $PBT_1$ used for polyp tip detection, the 3D box detector $PBT_2$ contains more structural information within a larger neighboring spatial span. The trained 3D box detector $PBT_2$ is used to detect voxels within the polyp by classifying voxels along each polar coordinate axis as polyp interior or polyp exterior voxels. For each voxel, a polyp interior class-conditional probability is calculated representing the probability that the voxel is a polyp interior voxel.

At step 710, the polyp surface boundary is detected using boosted 1D curve parsing and stacking. In order to detect the polyp boundary, this step is treated as a statistical curve parsing problem of finding polyp/nonpolyp breaking points on 1D curves. Given the output probabilities from the polyp interior/exterior detection (step 212), another layer of boundary boosting learning is applied, based on the theory of stacked generality. This is equivalent to learning a new boundary point classifier in the embedded, semantic space learned by the 3D box detector (as a wrapped) in the previous step. The boundary point classifier is trained as a PBT using 1D curve parsing based features based on the probabilities determined for voxels by the 3D box detector, such as probability count features and probability gap features. The resulting classifier is denoted herein as $PBT_3$.

Using the trained classifier $PBT_3$, a new probability value $P_{ij}$ is calculated for each voxel $v_{ij}$ on the local polar coordinate axes by evaluating forward and backward probability arrays $A_f(\rho_{ij})$ and $A_b(\rho_{ij})$ output by $PBT_2$. To determine a unique boundary point on any local polar coordinate axis i, $v_{ik_i}$ is selected with $\rho_{ik_i}=\max\{\rho_{i1}, \rho_{i2}, \rho_{i3}, \ldots, \rho_{ij}, \ldots\}$. Accordingly, a boundary voxel $v_{ik_i}$ is detected for each polar coordinate axis by the trained classifier $PBT_3$, and the set of boundary voxels define a boundary of the polyp.

At step 712, the segmented polyp surface boundary is smoothed. Assuming that the selection of each $\mu_{ik_i}$ is solely based on $\{\rho_{i1}, \rho_{i2}, \rho_{i3}, \ldots, \rho_{ij}, \ldots\}$ and independent with respect to the formation on other axes, the final polyp segmentation boundary will be rugged by sequentially connecting $v_{1k_1}, v_{2k_2}, \ldots$, on all axes of the local polar coordinates. For smoothness, these boundary decisions can be assembled using Gaussian blurring over their polar coordinates values $PC(v_{1k_1}), PC(v_{2k_2}), \ldots$, according to neighborhoods of successive axes. Alternatively, Viterbi-like dynamic programming can be utilized to solve this sequential smoothing problem with a looped trellis structure. Another possible smoothing solution is loopy belief propagation, which treats the local polar coordinates as a general looped 2D graph. Gaussian blurring is indeed a spatially homogenous smoothing filter, while Viterbi and loopy belief propagation are non-homogenous functions by building pairwise content-sensitive potential functions. All three smoothing approaches function as assemblers of propagating 1D axis segmentations across neighboring axes in polar coordinates.

Figure 11:
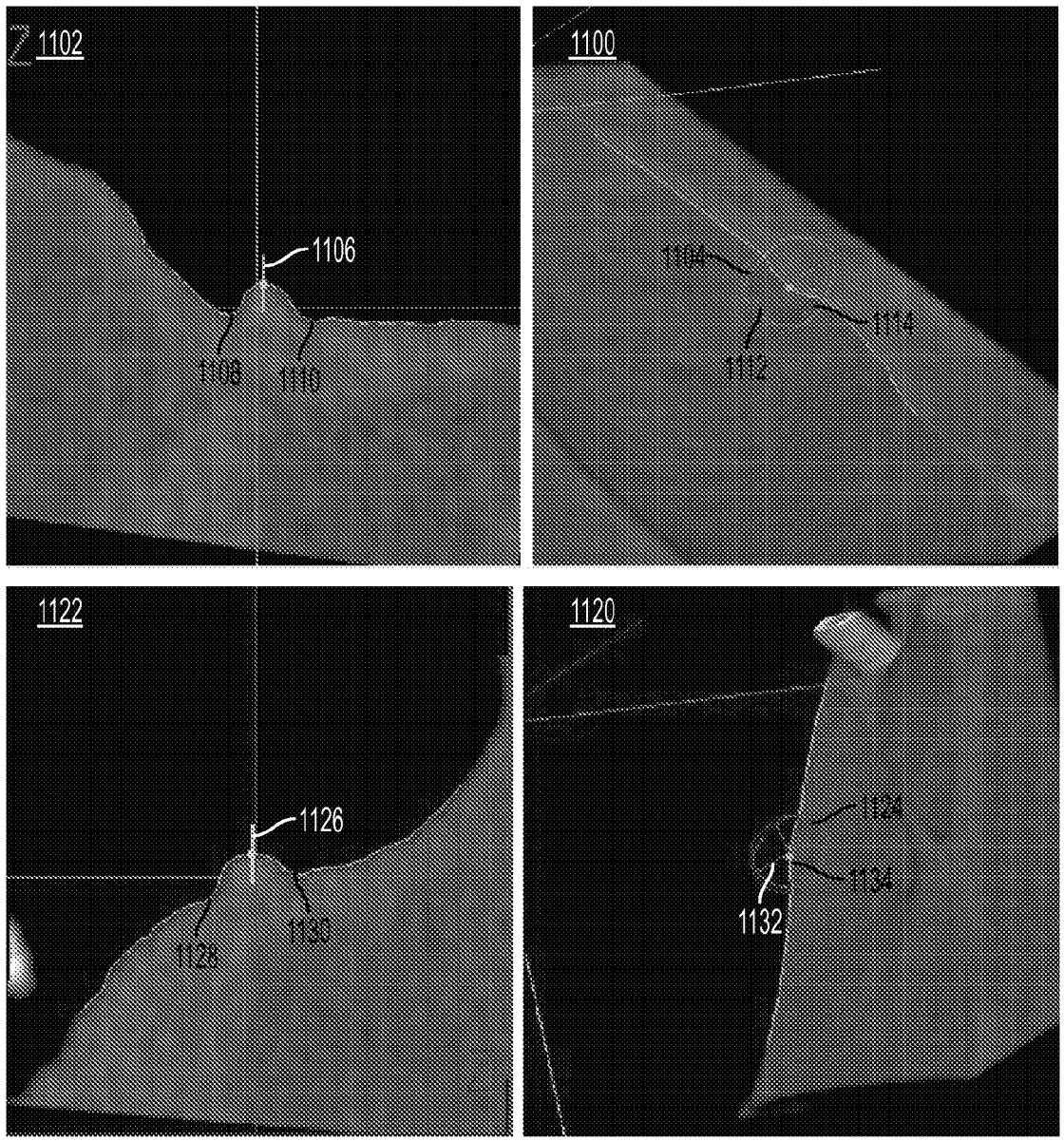
FIG. 11 illustrates illustrative displayed polyp segmentation results.

The method of FIG. 7 results in a smoothed segmented polyp boundary. Returning to FIG. 6, at step 606, the segmented polyp is displayed in the CTC volume in the interface. According to possible implantation, the interface can display the CTC volume with the segmented volume by displaying 2D radial cutting planes corresponding to axes of the local polar coordinate system fit to the colon surface. The interface can also display a 3D view of the segmented polyp. FIG. 11 illustrates illustrative displayed polyp segmentation results. As illustrated in FIG. 11, images 1100 and 1120 are 3D views of different CTC volumes, and images 1102 and 1122 are radial cutting planes of the CTC volumes of 1100 and 1120, respectively. Segmented polyp boundaries 1104 and 1124 are shown in images 1100 and 1120, respectively. The detected polyp tip 1106, as well as polyp boundary points 1108 and 1110 are shown in image 1102. Similarly, the detected polyp tip 1126, as well as polyp boundary points 1128 and 1130 are shown in image 1122. Two main polyp axes 1112 and 1114 for polyp dimensioning the segmented polyp boundary 1104 are shown in image 1100, and two main axes 1132 and 1134 for dimensioning the segmented polyp boundary 1124 are shown in image 1120.

Returning to FIG. 6, at step 608 a user determined whether he is satisfied with the polyp segmentation. If the user is not satisfied the method proceeds to step 610, where the user can modify the segmentation using the interface. If the user is satisfied with the polyp segmentation, the method proceeds to step 612.

At step 610, the user modifies the detected polyp boundary points on the local polar coordinate axes or the detected polyp tip using the interface. Accordingly, the interface receives a user input modifying the polyp boundary points or the detected polyp tip. As shown in FIG. 11, the user can view the segmentation results using 2D radial cutting planes corresponding to the local polar coordinate axes. Using the controls (e.g., FIG. 4) of the interface the user can navigate the radial cutting planes of a segmented CTC volume, and manually edit or modify the segmentation results. The user can move the position of the detected polyp tip or modify positions of polyp boundary voxels by clicking and dragging with an input device, such as a mouse, in order to correct mistakes or inaccuracies in the automatic polyp segmentation.

Once the user modifies either the detected polyp tip or the detected boundary points, the polyp is re-segmented in the CTC volume based on the modifications. If the polyp tip is modified, it is possible that the segmentation method can be performed again with the user modified polyp tip used in place of the result of the 3D point detector. If the user modifies one or more polyp boundary points on polar coordinate axes, it is possible that the modified boundary points be kept to define the polyp boundary with the non-modified boundary points, and the smoothing step of the automatic segmentation is performed to smooth the polyp boundary including the modified boundary points.

Figure 12:
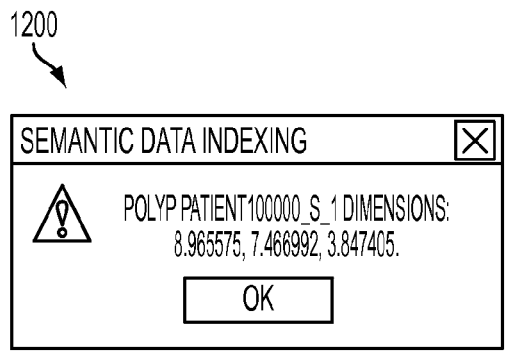
FIG. 12 illustrates exemplary polyp measurement results.

At step 612, once the user is satisfied with the polyp segmentation results that are displayed by the interface, the interface automatically measured the dimensions of the segmented polyp. It is possible that the dimensioning of the polyp be performed in response to a user input requesting polyp measurement. The polyp dimensions can be calculated by detecting three orthogonal polyp axes of the segmented polyp. After the polyp boundary is segmented for a polyp, a set of positive polyp surface voxels (with their associated probabilities $\rho$) inside the segmented polyp boundary can be enumerated. It is then straightforward to calculate the polyp dimensions. A pair of positive voxels $v^{11}$, $v^{12}$ are detected with the maximal Euclidean distance from each other to define a first polyp axis. Using the distance $dist(v^{11}, v^{12})$ as the estimated polyp size, other pairs of voxels $v^2$, $v^2$ that are orthogonal to $v^{11}$, $v^{12}$ (i.e., $(v^{2'}, v^{2''}) \oplus (v^{11}, v^{12}) = 0$). A pair of voxels $v^{21}, v^{22}$ are then selected from the orthogonal voxels $v^2, v^2$ with the maximal Euclidean distance from each other as the second polyp axis. A third polyp axis is then calculated by similarly calculating a third orthogonal axis. The detected polyp axes give the size of the polyp in three dimensions. The polyp dimensions can be output by the interface. FIG. 12 illustrates exemplary polyp measurement results. As illustrated in FIG. 12, dialog window 1200 outputs measurements for three dimensions of a segmented 3D polyp boundary. Dialog window 1200 shows the polyp name, identity, and 3D size values for the polyp.

In addition to being displayed by the interface, such as on a display device of a computer system, the segmented polyp boundary and the calculated polyp size measurements can also be output by being stored on a storage, memory, or other computer readable medium. A physician can use such polyp segmentation and measurement results for assisting with polyp annotation, as well as diagnostic and medical purposes, for example for polyp removal or diagnosis of colon cancer.

Figure 13:
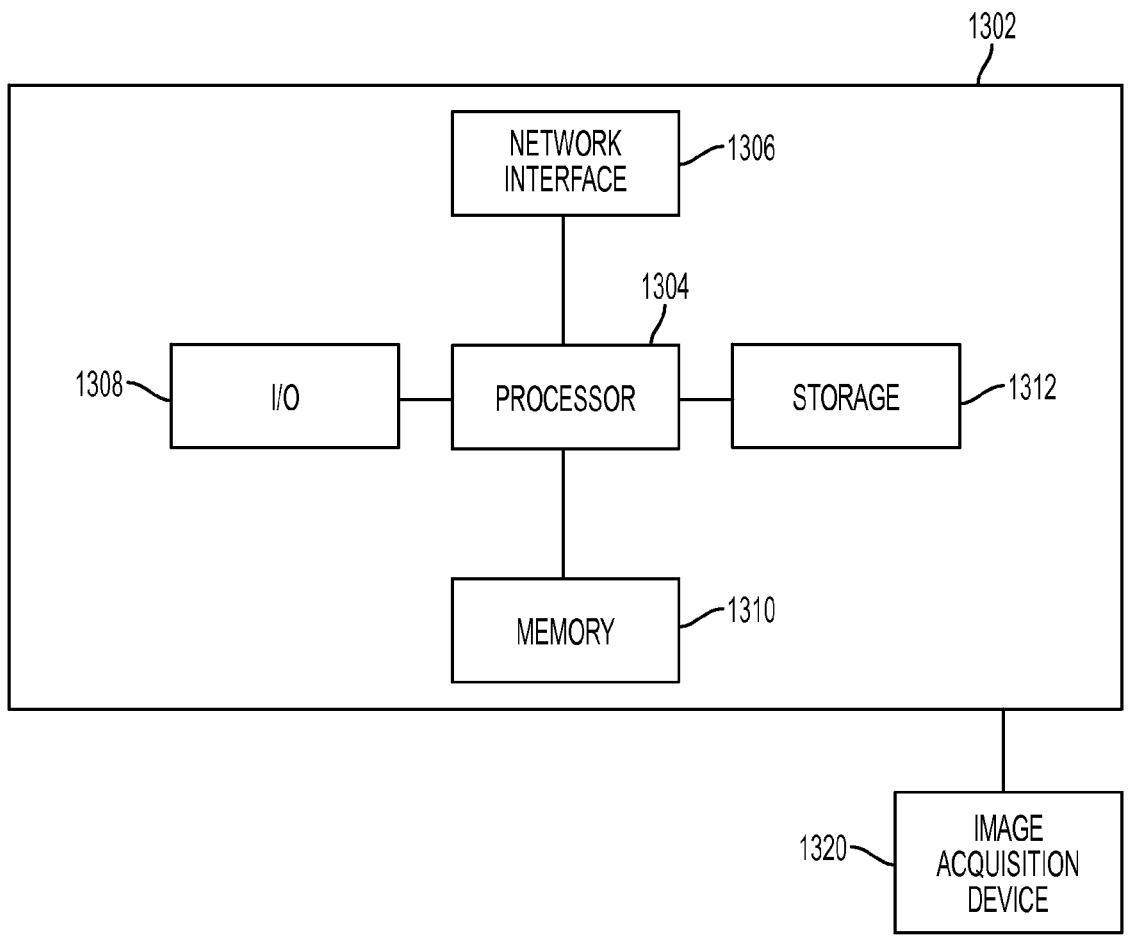
FIG. 13 is a high level block diagram of a computer capable of implementing the present invention.

The above-described polyp annotation, segmentation, and measurement methods, as well as the above-described polyp annotation, segmentation, and measurement interface may be implemented on a computer using well-known computer processors, memory units, storage devices, computer software, and other components. A high level block diagram of such a computer is illustrated in FIG. 13. Computer 1302 contains a processor 1304 which controls the overall operation of the computer 1302 by executing computer program instructions which define such operation. The computer program instructions may be stored in a storage device 1312, or other computer readable medium (e.g., magnetic disk), and loaded into memory 1310 when execution of the computer program instructions is desired. Thus, the steps of the method of FIGS. 6 and 7, as well as the user interface show in FIGS. 1 and 4, may be defined by the computer program instructions stored in the memory 1310 and/or storage 1312 and controlled by the processor 1304 executing the computer program instructions. Furthermore, the classifiers used in the above-described polyp segmentation method and the segmentation results achieved by the above described methods can be stored in the memory 1310 and/or storage 1312. An image acquisition device 1320, such as a CT scanning device, can be connected to the computer 1302 to input 3D CTC volumes to the computer 1302. It is possible to implement the image acquisition device 1320 and the computer 1302 as one device. It is also possible that the image acquisition device 1320 and the computer 1302 communicate wirelessly through a network. The computer 1302 also includes one or more network interfaces 1306 for communicating with other devices via a network. The computer 1302 also includes other input/output devices 1308 that enable user interaction with the computer 1302 (e.g., display, keyboard, mouse, speakers, buttons, etc.) such input/output devices 1308 can be used to interact with the above described user interface being executed on the computer 1302. One skilled in the art will recognize that an implementation of an actual computer could contain other components as well, and that FIG. 13 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A method for providing an interface for polyp annotation, segmentation, and measuring in computed tomography colonography (CTC) volumes, comprising:

receiving an initial polyp location in a CTC volume;
automatically segmenting a polyp in the CTC volume based on the initial polyp location by:
detecting a polyp tip in a neighborhood of the initial polyp location,
fitting a local polar coordinate system to a colon surface in the CTC volume based on the detected polyp tip, the local polar coordinate system including a plurality of axes,
detecting polyp interior and polyp exterior voxels along each of the plurality of axes of the local polar coordinate system, and
segmenting a boundary of the polyp in the CTC volume by detecting a boundary voxel for each of the plurality of axes of the local polar coordinate system based on the detected polyp interior and polyp exterior voxels;
displaying the segmented polyp in the CTC volume in a user interface;
receiving a user input via the user interface to modify the segmented polyp; and
re-segmenting the segmented polyp based on the received user input.

2. The method of claim 1, wherein said step of receiving an initial polyp location in a CTC volume comprises:
receiving the CTC volume; and
receiving a user input via the user interface identifying the initial polyp location.

3. The method of claim 1, wherein said step of receiving an initial polyp location in a CTC volume comprises:
detecting the initial polyp location in the CTC volume using a computer aided detection (CAD) system.

4. The method of claim 1, wherein said step of detecting a polyp tip comprises:
detecting polyp tip voxel candidates from colon surface voxels of the CTC using a trained 3D point detector;
clustering the polyp tip candidate voxels into a plurality of clusters;
calculating a fitness score for each of the clusters based on probabilities determined by the 3D point detector for the polyp tip voxel candidates in each cluster;
determining the geometric mean of the cluster with the maximal fitness score; and
projecting the geometric mean to a voxel on the colon surface.

5. The method of claim 4, wherein the trained 3D point detector is a probabilistic boosting tree (PBT) classifier trained using axis-based steerable features.

6. The method of claim 1, wherein said step of fitting a local polar coordinate system to a colon surface in the CTC volume based on the detected polyp tip comprises:
generating a colon surface model in the CTC volume; and
fitting the local polar coordinate system to the colon surface model with an origin of the local polar coordinate system at the detected polyp tip.

7. The method of claim 6, further comprising:
displaying the colon surface model in the user interface.

8. The method of claim 1, wherein said step of detecting polyp interior and polyp exterior voxels along each of the plurality of axes of the local polar coordinate system comprises:
determining a probability of a voxel being in the polyp for each voxel along each axes of the local polar coordinate system using a trained 3D box detector.

9. The method of claim 8, wherein the trained 3D box detector is a probabilistic boosting tree (PBT) classifier trained using box-based steerable features.

10. The method of claim 8, wherein said step of segmenting a boundary of a polyp in the CTC volume by detecting a boundary voxel for each of the plurality of axes of the local polar coordinate system based on the detected polyp interior and polyp exterior voxels comprises:
detecting a boundary voxel for each axis of the local polar coordinate system based on the probabilities determined by the trained 3D box detector by boosted 1D curve parsing using a trained classifier; and
stacking the detected boundary voxels to generate the boundary of the polyp.

11. The method of claim 10, wherein the trained classifier is a probabilistic boosting tree (PBT) classifier trained using probability count features and probability gap features based on the probabilities determined by the 3D box detector.

12. The method of claim 10, wherein said step of receiving a user input via the user interface to modify the segmented polyp comprises:
receiving a user input via the user interface adjusting a position of at least one boundary voxel of the segmented polyp boundary.

13. The method of claim 12, wherein said step of re-segmenting the segmented polyp based on the received user input comprises:
smoothing the segmented boundary with the adjusted position of the at least one boundary voxel.

14. The method of claim 1, wherein said step of receiving a user input via the user interface to modify the segmented polyp comprises:
receiving a user input via the user interface adjusting a position of the detected polyp tip.

15. The method of claim 1, wherein said step of automatically segmenting a polyp in the CTC volume based on the initial polyp location further comprises:
smoothing the segmented boundary of the polyp.

16. The method of claim 1, wherein said step of displaying the segmented polyp in the CTC volume in a user interface comprises:
displaying cutting planes of the CTC volume corresponding to the axes of the local polar coordinate system in the user interface.

17. The method of claim 1, further comprising:
measuring a size of the re-segmented polyp in three dimensions.

18. The method of claim 17, wherein said step of measuring a size of the re-segmented polyp in three dimensions comprises:
detecting first, second, and third polyp orthogonal axes in the re-segmented polyp.

19. An apparatus for providing an interface for polyp annotation, segmentation, and measuring in computed tomography colonography (CTC) volumes, comprising:
means for receiving an initial polyp location in a CTC volume;
means for segmenting a polyp in the CTC volume based on the initial polyp location, comprising:
means for detecting a polyp tip in a neighborhood of the initial polyp location,
means for fitting a local polar coordinate system to a colon surface in the CTC volume based on the detected polyp tip, the local polar coordinate system including a plurality of axes,
means for detecting polyp interior and polyp exterior voxels along each of the plurality of axes of the local polar coordinate system, and
means for segmenting a boundary of a polyp in the CTC volume by detecting a boundary voxel for each of the plurality of axes of the local polar coordinate system based on the detected polyp interior and polyp exterior voxels;
means for displaying the segmented polyp in the CTC volume;
means for receiving a user input to modify the segmented polyp; and
means for re-segmenting the segmented polyp based on the received user input.

20. The apparatus of claim 19, wherein said means for receiving an initial polyp location in a CTC volume comprises:
means for receiving a user input identifying the initial polyp location.

21. The apparatus of claim 19, wherein said means for receiving a user input to modify the segmented polyp comprises:
means for receiving a user input adjusting a position of at least one boundary voxel of the segmented polyp boundary.

22. The apparatus of claim 19, wherein said means for receiving a user input to modify the segmented polyp comprises:
  means for receiving a user input adjusting a position of the detected polyp tip.

23. The apparatus of claim 19, wherein said means for displaying the segmented polyp in the CTC volume comprises:
  means for displaying cutting planes of the CTC volume corresponding to the axes of the local polar coordinate system.

24. The apparatus of claim 19, further comprising:
  means for measuring a size of the re-segmented polyp in three dimensions.

25. A non-transitory computer readable medium encoded with computer executable instructions for providing an interface for polyp annotation, segmentation, and measuring in computed tomography colonography (CTC) volumes, the computer executable instructions defining steps comprising:
  receiving an initial polyp location in a CTC volume;
  automatically segmenting a polyp in the CTC volume based on the initial polyp location by:
    detecting a polyp tip in a neighborhood of the initial polyp location,
    fitting a local polar coordinate system to a colon surface in the CTC volume based on the detected polyp tip, the local polar coordinate system including a plurality of axes,
    detecting polyp interior and polyp exterior voxels along each of the plurality of axes of the local polar coordinate system, and
  segmenting a boundary of the polyp in the CTC volume by detecting a boundary voxel for each of the plurality of axes of the local polar coordinate system based on the detected polyp interior and polyp exterior voxels;
  displaying the segmented polyp in the CTC volume in a user interface;
  receiving a user input via the user interface to modify the segmented polyp; and
  re-segmenting the segmented polyp based on the received user input.

26. The non-transitory computer readable medium of claim 25, wherein the computer executable instructions defining the step of displaying the segmented polyp in the CTC volume in a user interface comprise computer executable instructions defining the step of:
  displaying cutting planes of the GIG volume corresponding to the axes of the local polar coordinate system in the user interface.

27. The non-transitory computer readable medium of claim 25, further comprising computer executable instructions defining the step of:
  measuring a size of the re-segmented polyp in three dimensions.

* * * * *